United States Patent
Muhlsteff et al.

(10) Patent No.: US 10,271,751 B2
(45) Date of Patent: Apr. 30, 2019

(54) MONITORING THE BLOOD PRESSURE OF A PATIENT

(75) Inventors: Jens Muhlsteff, Aachen (DE); Geert Guy Georges Morren, Tienen (BE); Xavier Louis Marie Antoine Aubert, Brussels (BE)

(73) Assignee: KONINKLIJKE PHILIPS N.V., Eindoven (NL)

( * ) Notice: Subject to any disclaimer, the term of this patent is extended or adjusted under 35 U.S.C. 154(b) by 1432 days.

(21) Appl. No.: 13/059,133

(22) PCT Filed: Aug. 12, 2009

(86) PCT No.: PCT/IB2009/053565
§ 371 (c)(1),
(2), (4) Date: Feb. 15, 2011

(87) PCT Pub. No.: WO2010/020914
PCT Pub. Date: Feb. 25, 2010

(65) Prior Publication Data
US 2011/0144456 A1 Jun. 16, 2011

(30) Foreign Application Priority Data
Aug. 19, 2008 (EP) ..................................... 08105077

(51) Int. Cl.
*A61B 5/0285* (2006.01)
*A61B 5/021* (2006.01)
(Continued)

(52) U.S. Cl.
CPC ............ *A61B 5/0285* (2013.01); *A61B 5/022* (2013.01); *A61B 5/02125* (2013.01); *A61B 5/0295* (2013.01); *A61B 5/7285* (2013.01)

(58) Field of Classification Search
CPC ........... A61M 2230/30; A61B 5/02125; A61B 5/0285; A61B 5/022; A61B 5/02; A61B 5/02108
(Continued)

(56) References Cited

U.S. PATENT DOCUMENTS 6,569,094 B2 5/2003 Suzuki et al.
6,763,256 B2 7/2004 Kimball
(Continued)

FOREIGN PATENT DOCUMENTS

CN 101234016 A1 6/2008
EP 0772998 5/1997
(Continued)

OTHER PUBLICATIONS

Lin et al., Estimation of Beat-to-Beat Systolic Blood Pressure Using Pulse Arrival Time and Pulse Width Derived from the Photoplethysmogram, 26th Annual International Conference of the IEEE EMBS, San Francisco, CA, Sep. 2004, pp. 3456-3485.*

*Primary Examiner* — Puya Agahi

(57) ABSTRACT

A method for monitoring the blood pressure of a patient, comprising the following steps: determining a pulse arrival time signal from the patient 2 based on the pulse wave velocity method; determining an accelerometer signal from the patient 2; and triggering an additional measure or deriving a blood pressure value, taking into account the pulse arrival time signal and a DC component of the accelerometer signal. In this way, a possibility for monitoring the blood pressure of a patient is provided with which false alarms and/or unnecessary additional cuff-based blood pressure measurements can be avoided.

20 Claims, 1 Drawing Sheet

(51) Int. Cl.
*A61B 5/022* (2006.01)
*A61B 5/00* (2006.01)
*A61B 5/0295* (2006.01)

(58) Field of Classification Search
USPC .................. 600/301, 481, 490, 500, 504
See application file for complete search history.

(56) References Cited

U.S. PATENT DOCUMENTS

| | | |
|---|---|---|
| 6,783,498 B2 * | 8/2004 | Sackner et al. ............... 600/481 |
| 7,566,307 B2 | 7/2009 | Inukai et al. |
| 7,974,689 B2 * | 7/2011 | Volpe et al. ..................... 607/6 |
| 2002/0183627 A1 | 12/2002 | Nishii et al. |
| 2004/0077958 A1 * | 4/2004 | Kato et al. .................. 600/490 |
| 2005/0209512 A1 * | 9/2005 | Heruth et al. ................ 600/301 |
| 2005/0251059 A1 | 11/2005 | Kim |
| 2006/0200011 A1 * | 9/2006 | Suzuki et al. ................ 600/301 |
| 2007/0016086 A1 | 1/2007 | Inukai et al. |
| 2007/0055163 A1 * | 3/2007 | Asada et al. .................. 600/485 |
| 2007/0142730 A1 | 6/2007 | Laermer et al. |
| 2007/0142868 A1 | 6/2007 | Moon et al. |
| 2009/0062667 A1 * | 3/2009 | Fayram et al. ............... 600/486 |

FOREIGN PATENT DOCUMENTS

| | | |
|---|---|---|
| JP | H08317920 A | 12/1996 |
| JP | 2004174147 A | 6/2004 |
| WO | 2006124768 A1 | 11/2006 |
| WO | 2007026281 A1 | 3/2007 |

\* cited by examiner

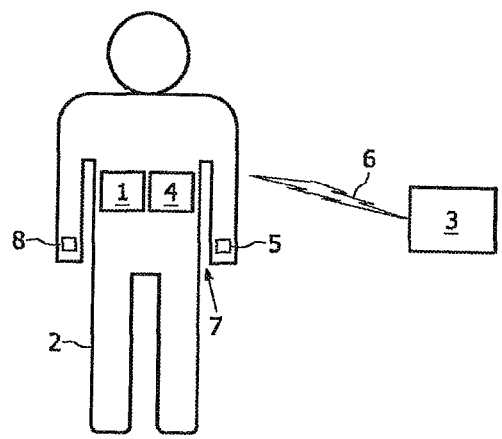
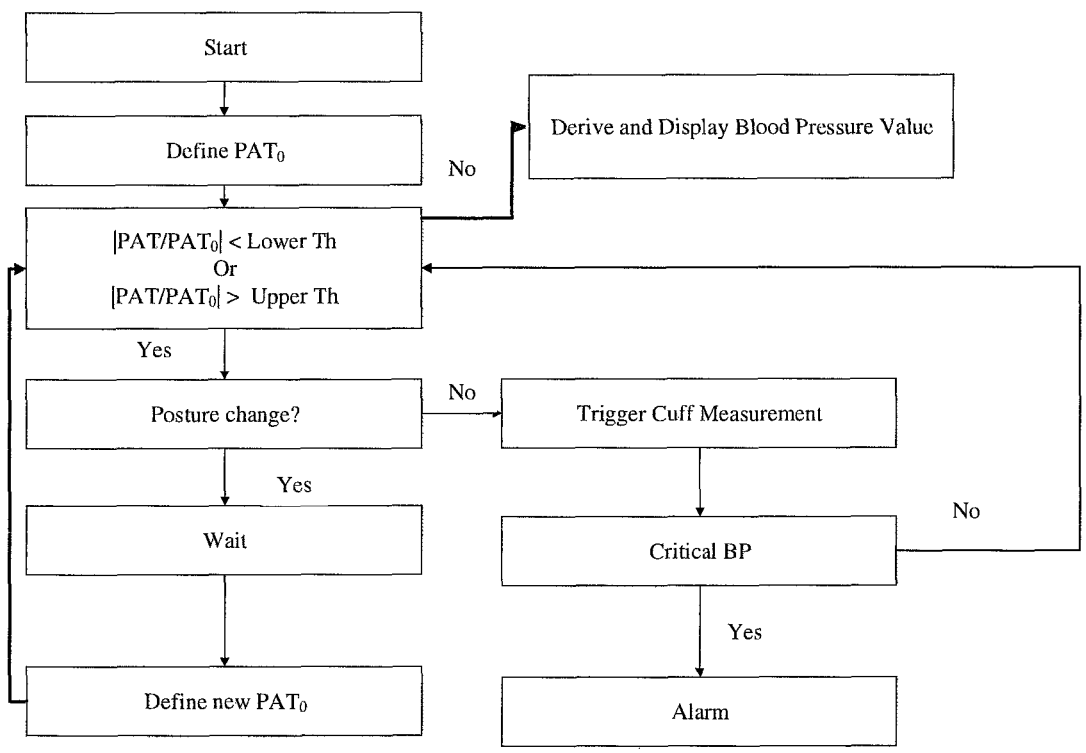
FIG. 2

MONITORING THE BLOOD PRESSURE OF A PATIENT

FIELD OF THE INVENTION

The invention relates to the field of monitoring the blood pressure of a patient, and especially to avoiding false alarms when monitoring the blood pressure.

BACKGROUND OF THE INVENTION

Blood pressure measurements in clinical setting are conventionally mainly based on the sphygmo-manometric occlusive arm-cuff, which is clumsy, uncomfortable and only allows for intermittent measurements at intervals of several minutes. Hence, there is a strong interest by the medical community in new technologies, which provide timely detection of critical changes of a patient's blood circulation status. A technical approach for early detection of critical blood pressure changes is based on the pulse wave velocity (PWV) technique, where surrogate markers of blood pressure are typically derived from a continuously monitored ECG waveform and plethysmograph like the signal of a single wavelength of from a SpO2 sensor. The measurement of the pulse wave velocity offers the opportunity to derive significant changes of arterial blood pressure at heart-beat frequency without applying an external pressure. It is common practice to use the pulse arrival time (PAT), which is defined as the time-delay between the R-peak of the QRS wave from the ECG and the arrival of the arterial pulse wave at the periphery, e.g. measured by a plethysmograhic sensor.

Conventionally, whenever a significant change in blood circulation is identified based on a measurement of the pulse arrival time from the ECG and the plethysmograhic sensor, a standard cuff-based blood pressure measurement is triggered automatically to confirm the change in blood pressure and to let the practitioner know it, when the patient's blood pressure is falling/increasing to critical level. However, in this way still a great number of cuff-based blood pressure measurement is triggered which would not have been necessary since actually no severe change in blood pressure of the patient has occurred.

SUMMARY OF THE INVENTION

It is an object of the invention to provide a method and a system for monitoring the blood pressure of a patient with which false alarms and/or unnecessary additional cuff-based blood pressure measurements can be avoided.

This object is achieved by a method for monitoring the blood pressure of a patient, comprising the following steps:
  determining a pulse arrival time signal from the patient based on the pulse wave velocity method;
  determining an accelerometer signal from the patient; and
  triggering an additional measure or deriving a blood pressure value, taking into account the pulse arrival time signal and a DC component of the accelerometer signal.

This means that, according to the invention, a DC component of the accelerometer signal is determined. In this way, effects on the pulse arrival time which are due to different postures and not because of a changing circulatory state of the patient can be taken into account. Especially, according to the invention, a blood pressure value can be derived on the basis of the determined pulse arrival time and a DC component of the accelerometer signal which means that a blood pressure value is determined which is corrected by the posture effect on the pulse arrival time detected by the DC component of the accelerometer signal. Alternatively, based on the pulse arrival time and the DC component of the accelerometer signal, an additional measure can be triggered which means that in case the pulse arrival time and/or the DC component of the accelerometer signal fulfill a predefined condition, further measures can be taken. What such additional measures can be, is set out in detail in the following.

With respect to taking an additional measure, according to a preferred embodiment of the invention, before triggering the additional measure, the value of the pulse arrival time signal is compared with at least one predefined pulse arrival time threshold value, and the additional measure is only taken if the value of the pulse arrival time signal exceeds or under-runs the predefined pulse arrival time threshold value.

This means that an additional measure is only taken when the pulse arrival time becomes longer or shorter than a predefined threshold value, respectively, which means that the blood pressure might have fallen or risen over an acceptable value, respectively. With respect to this, it is possible to have only one threshold value, which then is an upper or a lower threshold value. However, it is preferred that two threshold values are used, i.e. an upper threshold value and a lower threshold value. Furthermore, according to a preferred embodiment of the invention, the upper threshold value and/or the lower threshold value is dependent on the heart rate.

With respect to this, it is further preferred that the additional measure is checking for a posture change based on a change of a DC component of the accelerometer signal. This provides for the following possibility:

In case a posture change is actually detected since a DC component of the accelerometer signal has changed, it is waited for an equilibration of the blood pressure regulation of the patient in this new posture. After equilibration, a new threshold value for the pulse arrival time can be determined, taking into consideration the effects of the new posture on the blood pressure.

However, should no posture change be detected, the change of the value of the pulse arrival time is probably due to an actual change of the blood pressure. In this case, according to a preferred embodiment of the invention, the additional measure is a cuff-based measurement of the blood pressure of the patient. In this way, the blood pressure can be detected in an even more reliable way. Especially, in case the blood pressure value of the cuff-based blood pressure measurement exceeds a predefined blood pressure threshold value, according to a preferred embodiment of the invention, a subsequent alarm is triggered.

Though above mentioned method might be more reliable, according to another preferred embodiment of the invention, the additional measure is a direct alarm which means that in case that the value of the pulse arrival time signal exceeds or under-runs the predefined pulse arrival time threshold value and no posture change is detected based on the DC component of the accelerometer signal, an alarm is directly triggered without further performing a cuff-based blood pressure measurement.

Moreover, according to another preferred embodiment of the invention, the step of deriving the blood pressure value taking into account the pulse arrival time signal and the DC component of the accelerometer signal further comprises the step of determining the blood pressure value based on pre-calibrated values for pulse arrival time signal vs. DC component of the accelerometer signal. With respect to this, it is especially preferred that pre-calibrated values of the blood pressure for pulse arrival time signal vs. DC components of the accelerometer signal is provided in a look-up table which has been generated in a preceding calibration procedure. Alternatively, an analytical correction function for the blood pressure on the basis of values for pulse arrival time signal vs. DC component of the accelerometer signal can be provided. This preferred embodiment of the invention provides for an absolute determination of the blood pressure of the patient corrected by the effects of different postures of the patient on the PAT measure.

Further, according to a preferred embodiment of the invention, the step of deriving a blood pressure signal from the patient based on the pulse wave velocity-method comprises the steps of deriving an ECG signal from the patient, and deriving a pulse wave signal from the patient. With respect to this, it is especially preferred that the step of deriving a pulse wave signal from the patient comprises the step of deriving a pulse wave signal from the patient, preferably a plethysmographic signal e.g. by optical or bioimpedance means.

Above-mentioned object is further addressed by a system for monitoring the blood pressure of a patient, comprising:
a pulse wave velocity unit adapted for determining a pulse arrival time signal from the patient based on the pulse wave velocity method;
an accelerometer adapted for determining an accelerometer signal from the patient; and
a monitoring device adapted for triggering an additional measure or deriving a blood pressure value, taking into account the pulse arrival time signal and a DC component of the accelerometer signal.

Preferred embodiments of the system according to the invention relate to the preferred embodiments according to the method as described above.

In detail, according to a preferred embodiment of the invention, the system comprises a comparator which is adapted for comparing the value of the pulse arrival time signal with a predefined pulse arrival time threshold value. Further, according to a preferred embodiment of the invention, a cuff is provided which is adapted for a cuff-based measurement of the blood pressure of the patient.

Furthermore, according to a preferred embodiment of the invention, an alarm unit is provided which is adapted for triggering an alarm in case the blood pressure value of the cuff-based blood pressure measurement exceeds or falls below a predefined blood pressure threshold value or the pulse arrival time signal under-runs a predefined pulse arrival time threshold value.

Moreover, according to a preferred embodiment of the invention, a storage device is provided in which pre-calibrated values for pulse arrival time signal vs. DC component of the accelerometer signal are stored. Such pre-calibrated values can be provided in form of a look-up table or in form of an analytical function. According to another preferred embodiment of the invention, the pulse wave velocity unit comprises an ECG sensor and a pulse sensor, preferably adapted for deriving a plethysmographic signal from the patient.

In order to detect the posture of the patient, an additional sensor on the patient can be used. In this case, a separate acceleration sensor is attached to the patient and connected to the monitoring device. However, according to a preferred embodiment of the invention, an ECG-electrode with an integrated acceleration sensor is used. According to another preferred embodiment, an ECG-electrode connector with an integrated acceleration sensor is provided.

BRIEF DESCRIPTION OF THE DRAWINGS

These and other aspects of the invention will be apparent from and elucidated with reference to the embodiments described hereinafter.

In the drawings:
FIG. 1 is a schematical depiction of an embodiment of the invention; and
FIG. 2 is a flow diagram of another embodiment of the invention.

DETAILED DESCRIPTION OF EMBODIMENTS

As already stated above, PWV measurement is a promising approach, which offers the opportunity to derive significant changes of arterial blood pressure at a heart-beat frequency without applying an external pressure. For that, the pulse arrival time is determined, which is defined as the time-delay between the R-peak of the QRS wave from the ECG and the arrival of the arterial pulse wave at the periphery. This comprises the sum of the pre-ejection period (PEP) and the pulse transit time (PTT), both representing different underlying cardiovascular mechanisms:

$$PAT=PEP+PTT$$

More precisely, the PEP is a cardiac component covering the iso-volumic ventricular contraction stage while the PTT is a purely vascular component that can only be defined after the aortic valve opening. It was found that PEP is a good marker for blood pressure changes induced by physical stress. However, PEP is also sensitive to fluid shifts within the body induced by posture changes at constant blood pressure, which has to be taken into account for detecting accurately significant blood pressure changes. Further, it has been found that the known PEP effect causes a significant PAT change that is not associated with a blood pressure change. The observed PAT change for different postures is covered almost completely by the PEP changes. In order to compensate this effect, according to an embodiment of invention, the posture of the patient is detected.

In order to detect the posture of the patient, according to this preferred embodiment of the invention, an acceleration sensor 1 is attached to the patient 2 and connected to a monitoring device 3, which is schematically depicted in FIG. 1. The connection of the acceleration sensor 1 with the monitoring device 3 is a wireless connection 6. The patient's 2 posture is inferred from the DC-components, i.e. averages, of the acceleration signals, which contain information of the acceleration sensor's 1 orientation with respect to the earth gravity axis.

Since earth gravity creates a constant acceleration towards ground, its projection on the axis of the acceleration sensor 1 unveils the orientation of this axis and, hence, of the acceleration sensor 1. Thus, the patient 2 is considered to be standing when its trunk is upright, sitting when its trunk is slightly tilted backward, and lying when its trunk is roughly parallel to the ground. For a correct classification of the patient's 2 posture it is preferred to calibrate the system with a known posture. Further, for the actual blood pressure monitoring, according to the embodiment of the invention shown in FIG. 1, an ECG sensor 4 and a pulse wave sensor 5 for a plethysmographic measurement are provided in a conventional way for enabling a PWV measurement, the ECG sensor 4 and the pulse wave sensor 5 forming a pulse wave velocity unit 7. The ECG sensor 4 and the optical sensor 5 are both connected with the monitoring device via the wireless connection 6, too. Further, a cuff 8 for a conventional cuff-based blood pressure measurement is provided.

As shown in FIG. 1, a separate acceleration sensor 1 can be provided on the patient 2 in order to detect his posture. According to another embodiment, an ECG electrode with an integrated acceleration sensor can be used. Further, it is also possible to use an ECG-electrode connector with an integrated acceleration sensor.

Moreover, according to still another preferred embodiment of the invention, an automated normalization of the pulse arrival time (PAT) after detecting a posture change is applied: After a posture change has been detected, the continuously measured pulse arrival time is normalized for the new posture. This is done automatically, triggered by the detected posture change via the acceleration sensor signal, and a new reference PAT is determined. An according flow diagram for this embodiment of the invention is shown in FIG. 2.

According to the embodiment of the invention shown in FIG. 2 exemplified for detection of an critical blood pressure increase, at the beginning of the monitoring, a threshold value for the pulse arrival time ($PAT_0$) is determined, e.g. on the basis of the detected pulse arrival time average over a predefined duration. Further, when such a pulse arrival time value is observed which falls below the predefined threshold value, it is checked if a posture change of the patient was detected. If such a posture change was actually detected, it is waited until the blood pressure regulation process has equilibrated. Then, a new threshold value is defined based on an average of monitoring the pulse arrival time for a predefined duration. Then, it is further checked if the actual pulse arrival time observed under-runs the new threshold value. Then, the process described above may continue.

In case that, when checking for a posture change of the patient, it is detected that no posture change has occurred since the DC component of the accelerator signal has not changed, a cuff-based blood pressure measurement is triggered. If this cuff-based blood pressure measurement results in a critical blood pressure which exceeds a predefined threshold value, an alarm is generated. In case the cuff-based blood pressure value is not determined to be critical, it is continued with checking the actual pulse arrival time as described before.

Further, according to still another embodiment of the invention, before a monitoring period is started, a calibration procedure is performed for different postures of the patient providing the relation of PAT vs. postures, e.g. at several different angles. A look up-table is created by this procedure, which can be used in the monitoring period to compensate for PAT changes caused by posture changes. In addition, the blood pressure can be measured with a cuff to assess the blood pressure changes associated with the different postures, which allows a further refinement of the posture-related PAT corrections. Alternatively, PEP can be measured directly in different postures using for example a stethoscope for heart sound analysis or impedance cardiography.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for monitoring blood pressure of a patient, comprising the following steps:
    (a) determining a pulse arrival time signal from the patient with a pulse wave velocity unit based on a pulse wave velocity method;
    (b) determining an accelerometer signal from the patient with an accelerometer sensor after determining the pulse arrival time signal;
    (c) detecting a DC component of the accelerometer signal indicative of a posture of the patient with a monitoring device;
    (d) normalizing the pulse arrival time signal with a reference pulse arrival time value with the monitoring device by dividing the determined pulse arrival time signal by a reference pulse arrival time value to generate a normalized pulse arrival time signal;
    (e) comparing a value of the normalized pulse arrival time signal with predefined upper and lower pulse arrival time threshold values with the monitoring device;
    (f) determining if the value of the normalized pulse arrival time signal exceeds the upper reference threshold value or under-runs the lower reference threshold value with the monitoring device;
    (g) checking for a change in the posture of the patient based on a change of the DC component of the accelerometer signal;
    at least one of:
    (h) repeating steps (a)-(g) when the value of the normalized pulse arrival time signal exceeds or under-runs the predefined pulse arrival time threshold values;
    (i) in response to the normalized pulse arrival time signal exceeding or under-running the predefined pulse arrival time threshold values and the DC component change not being detected, at least one of:
        controlling an alarm to generate an alarm signal; and
        controlling a blood pressure cuff to measure the blood pressure of the patient, and
    (j) in response to the normalized pulse arrival time signal exceeding or under-running the predefined pulse arrival time threshold values and the DC component change being detected, updating the reference pulse arrival time value; and
    (k) deriving and displaying a blood pressure value with the monitoring device from the normalized pulse arrival time signal when the value of the normalized pulse arrival time signal does not exceed or under-run the predefined pulse arrival time threshold values.

2. The method according to claim 1, wherein the reference pulse arrival time threshold value is dependent on a heart rate.

3. The method according to claim 1, further including:
    with the monitoring device, in response to the normalized pulse arrival time signal exceeding or under-running the pulse arrival time threshold values and the posture change being detected, controlling the blood pressure cuff to make a cuff-based measurement of the blood pressure value of the patient.

4. The method according to claim 1, further including, with the monitoring device, at least one of:
   inputting the pulse arrival time signal and the DC component of the accelerometer signal into a look-up table which was pre-calibrated with blood pressure values to give the blood pressure value, the blood pressure value being based on the input pulse arrival time signal and the input DC component; or
   operating on the pulse arrival time signal and the DC component with an analytical correction function which was pre-calculated to provide a determination of the patient's blood pressure corrected for an effect of posture.

5. The method according to claim 1, wherein the step of determining the pulse arrival time signal from the patient based on the pulse wave velocity-method comprises the steps of deriving an electrocardiogram signal from the patient, and deriving a pulse wave signal from the patient.

6. The method according to claim 5, wherein the step of deriving the pulse wave signal from the patient comprises the step of deriving a plethysmographic signal.

7. An apparatus for monitoring blood pressure of a patient, comprising:
   a blood pressure cuff;
   an alarm unit in communication with the blood pressure cuff;
   a pulse wave velocity unit comprising an ECG sensor and an optical sensor adapted to generate a plethysmographic signal from the patient, the pulse wave velocity unit configured to determine a first measure including a pulse arrival time signal from the patient based on a pulse wave velocity method;
   an accelerometer configured to be attached to a torso of the patient and to determine a second measure including an accelerometer signal from the patient, the accelerometer signal including a component which is indicative of an orientation of the accelerometer and the patient torso with respect to an earth gravity axis; and
   a monitoring device wirelessly connected with the ECG sensor, the optical sensor, and the accelerometer, the monitoring device configured to adjust the pulse arrival time signal based on the orientation of the accelerometer and the patient torso and at least one of:
      trigger the pulse wave velocity unit to again determine the first measure and the accelerometer to again determine the second measure;
      derive a blood pressure value, based on the pulse arrival time signal;
      divide the measured pulse arrival time signal by a reference pulse arrival time value to generate a normalized pulse arrival time signal;
      compare the normalized pulse arrival time signal with upper and lower threshold values of a threshold;
      detect a change in a DC component of the accelerometer signal;
      in response to the normalized pulse arrival time signal being outside of the upper and lower threshold values of the threshold and the DC component change not being detected:
         control the blood pressure cuff to measure the blood pressure of the patient; and
         control the alarm unit to generate an alarm signal in response to the blood pressure measured by the blood pressure cuff is outside of the upper and lower values of a predefined alarm threshold; and
      in response to the normalized pulse arrival time signal being outside of the upper and lower threshold values of the threshold and the DC component change being detected, update the reference pulse arrival time value.

8. The apparatus according to claim 7, further including: a display which displays the blood pressure value.

9. The apparatus according to claim 7, wherein the monitoring device is further configured to operate on the pulse arrival time signal and the DC component with an analytical correction function which was pre-calibrated to provide a determination of the patient's blood pressure corrected for an effect of posture.

10. The apparatus according to claim 7, wherein the monitoring device is further configured to input the pulse arrival time signal and the DC component of the accelerometer signal into a look-up table which was pre-calibrated with blood pressure values to give the blood pressure value, the blood pressure value being based on the input pulse arrival time signal and the input DC component.

11. The apparatus according to claim 7, wherein the pulse wave velocity unit comprises an electrocardiogram sensor and a plethysmograph.

12. The method according to claim 1, further including:
   attaching the accelerometer to a torso of the patient such that the DC component is indicative of an orientation of the torso relative to an axis of earth gravity.

13. A method for monitoring blood pressure of a patient, comprising:
   with an electrocardiogram sensor and a plethysmograph, sensing blood flow of the patient and generating a pulse arrival time signal;
   with an accelerometer attached to the patient, generating an accelerometer signal indicative of patient motion;
   with a monitoring device,
      comparing the pulse arrival time signal normalized by being divided by a reference pulse arrival time value with upper and lower threshold values of a threshold and repeating the sensing and generating until the normalized pulse arrival time signal is outside of the upper and lower threshold values of the threshold;
      detecting a change in a DC component of the accelerometer signal;
      in response to the normalized pulse arrival time signal being outside of the upper and lower threshold values of the threshold and the DC component change not being detected, at least one of:
         controlling an alarm to generate an alarm signal; and
         controlling a blood pressure cuff to measure the blood pressure of the patient, and
      in response to the normalized pulse arrival time signal being outside of the upper and lower threshold values of the threshold and the DC component change being detected, updating the reference pulse arrival time value.

14. The method of claim 13, further including with the monitoring device:
   inputting the pulse arrival time signal and the DC component of the accelerometer signal into a look-up table which was pre-calibrated with blood pressure values to give a blood pressure value based on the input pulse arrival time signal and the input DC component.

15. The method according to claim 13, further including with the monitoring device:
   operating on the pulse arrival time signal and the DC component with an analytical correction function which was pre-calibrated to provide a determination of the patient's blood pressure corrected for an effect of posture.

16. A method for monitoring blood pressure of a patient, comprising:
- with an electrocardiogram sensor and a plethysmograph, sensing blood flow of the patient and generating a pulse arrival time signal;
- with an accelerometer attached to the patient, generating an accelerometer signal indicative of patient motion;
- with a monitoring device, one of:
  - inputting the pulse arrival time signal and the DC component of the accelerometer signal into a look-up table which was pre-calibrated with blood pressure values to give a blood pressure value based on the input pulse arrival time signal and the input DC component; and
  - operating on the pulse arrival time signal and the DC component with an analytical correction function which was pre-calibrated to provide a determination of the patient's blood pressure corrected for an effect of posture;
- comparing the pulse arrival time signal normalized by being divided by a reference pulse arrival time value with upper and lower threshold values of a threshold;
- detecting a change in a DC component of the accelerometer signal;
- in response to the normalized pulse arrival time signal exceeding or under-running the upper and lower threshold values of the threshold and the DC component change not being detected, at least one of:
  - controlling an alarm to generate an alarm signal; and
  - controlling a blood pressure cuff to measure the blood pressure of the patient, and
- in response to the normalized pulse arrival time signal exceeding or under-running the upper and lower threshold values of the threshold and the DC component change being detected, updating the reference pulse arrival time value.

17. The apparatus according to claim 7, wherein the normalized pulse arrival time signal is outside of a first threshold when the normalized pulse arrival time signal exceeds the upper threshold value or when the normalized pulse arrival time signal under-runs the lower threshold value.

18. The method according to claim 13, wherein the normalized pulse arrival time signal is outside of a first threshold when the normalized pulse arrival time signal exceeds the upper threshold value or when the normalized pulse arrival time signal under-runs the lower threshold value.

19. The method according to claim 16, wherein the threshold includes a first threshold with the upper threshold value and the lower threshold value, the normalized pulse arrival time signal being outside of the first threshold when the normalized pulse arrival time signal exceeds the upper threshold value or when the normalized pulse arrival time signal under-runs the lower threshold value.

20. The apparatus according to claim 7, wherein the monitoring device is further configured to derive a blood pressure value from the normalized pulse arrival time signal and the DC component of the accelerometer signal when the value of the normalized pulse arrival time signal does not exceed or under-run the reference pulse arrival time threshold value.

* * * * *